(12) United States Patent
Joos

(10) Patent No.: US 6,506,191 B1
(45) Date of Patent: Jan. 14, 2003

(54) OSTEOSYNTHETIC FASTENING DEVICE

(75) Inventor: Ulrich Joos, Münster (DE)

(73) Assignee: Medartis AG, Basel (CH)

( * ) Notice: Subject to any disclaimer, the term of this patent is extended or adjusted under 35 U.S.C. 154(b) by 0 days.

(21) Appl. No.: 09/763,558

(22) PCT Filed: Aug. 25, 1998

(86) PCT No.: PCT/CH98/00366

§ 371 (c)(1), (2), (4) Date: Feb. 22, 2001

(87) PCT Pub. No.: WO98/44849

PCT Pub. Date: Oct. 15, 1998

(51) Int. Cl.$^7$ .............................................. A61B 17/80
(52) U.S. Cl. .............................. 606/72; 606/60; 606/69
(58) Field of Search ........................ 606/60, 69, 70–73

(56) References Cited

U.S. PATENT DOCUMENTS

| | | | | |
|---|---|---|---|---|
| 1,025,008 A | * | 4/1912 | Miner ........................ | 606/71 |
| 5,108,399 A | * | 4/1992 | Eitenmuller et al. .......... | 606/77 |
| 5,352,229 A | * | 10/1994 | Goble et al. .................. | 606/72 |
| 5,728,127 A | * | 3/1998 | Asher et al. .................. | 606/61 |
| 5,947,968 A | * | 9/1999 | Rogozinski .................. | 606/61 |
| 6,015,410 A | * | 1/2000 | Tormala et al. ............... | 606/73 |
| 6,053,919 A | * | 4/2000 | Talos et al. ................... | 606/71 |

FOREIGN PATENT DOCUMENTS

| | | |
|---|---|---|
| DE | 2340880 | 3/1975 |
| DE | 4018273 | 1/1991 |
| DE | 9016507 | 2/1991 |
| WO | 9701991 | 1/1997 |

* cited by examiner

Primary Examiner—Nicholas D. Lucchesi
Assistant Examiner—Michael B. Priddy
(74) Attorney, Agent, or Firm—Selitto, Behr & Kim

(57) ABSTRACT

The device with a bone plate (1) and with a temporarily attachable retainer (100) is used for fixation of, in particular, fragments of a jaw bone. The bone plate (1) has a longitudinal guide slot (40) which is open at one end or closed at both ends. The retainer (100) comprises a disk (110) which engages partially over the bone plate (1) and in which a locking screw (120) sits preferably in a rotatable manner and secure against loss, said locking screw (120) being intended to be screwed into a bone fragment via the guide slot (40). At one end, the bone plate (1) advantageously has areas of members (30) comprising individual members which can be divided off to obtain the desired length, The device extends the possibilities of screwing the bone plate (1), so that better adaptability to the particular task is achieved, and also improved rigidity across the edge of the bone plate (1), while the elasticity of the latter across the surface can be increased by means of less material thickness. The as it were one-piece retainer simplifies handling. A fixing plate is provided for additionally stiffening the screwed-on bone plate (1) and/or for screwing it at one end. In a second embodiment, the retainer can be, screwed to the underlying bone fragment laterally outside the bone plate (1).

25 Claims, 6 Drawing Sheets

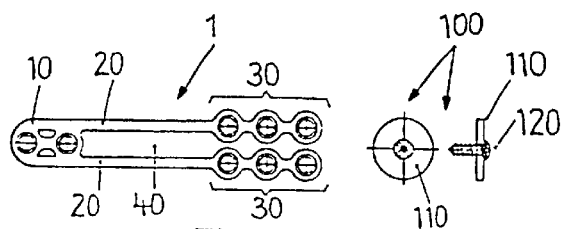
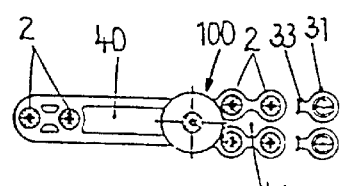
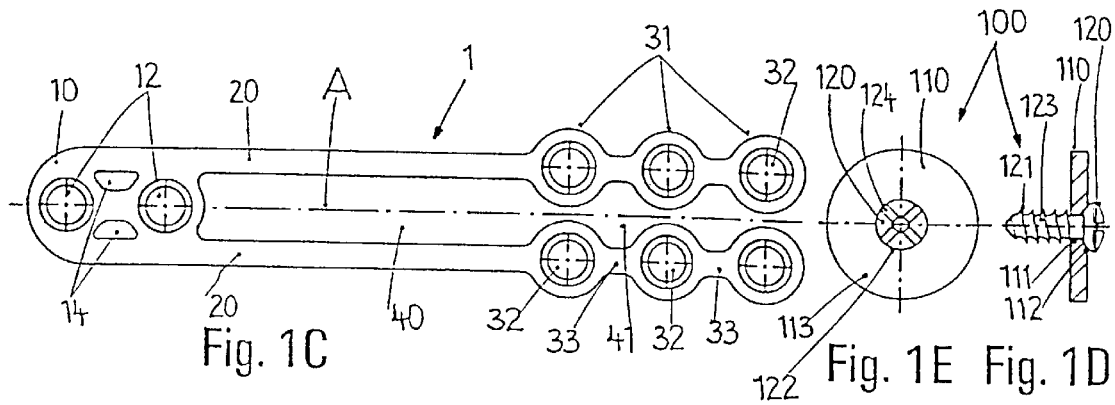
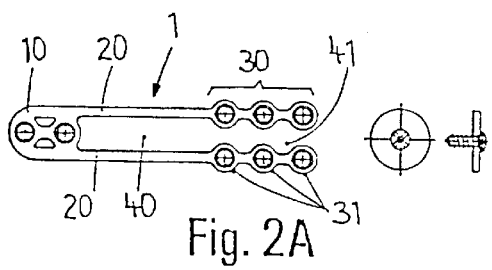
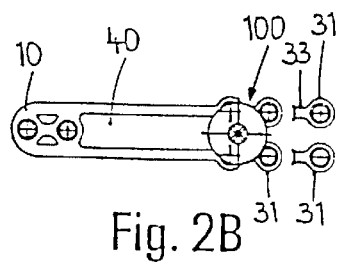
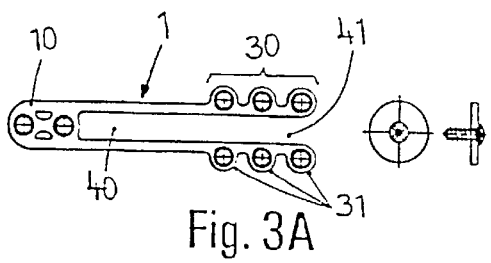
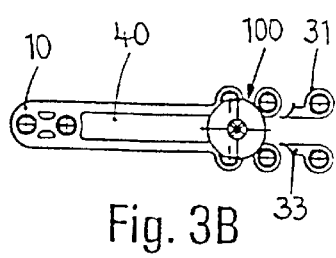

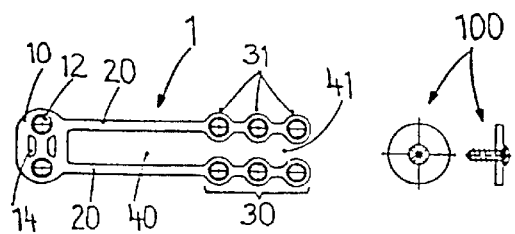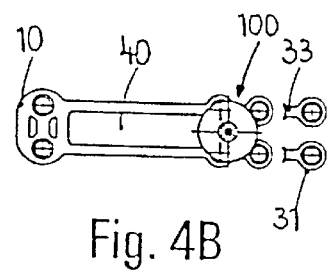
Fig. 4A  Fig. 4B
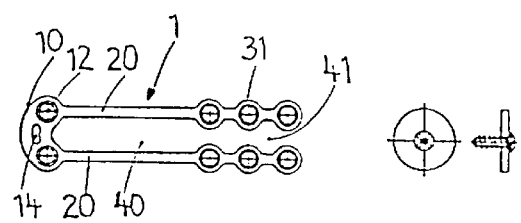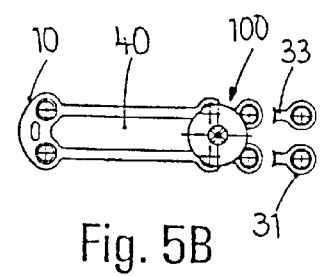
Fig. 5A  Fig. 5B
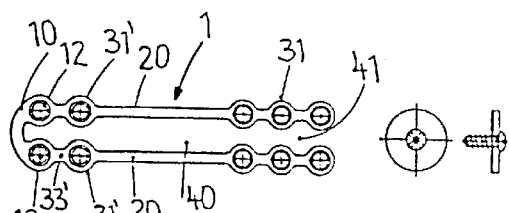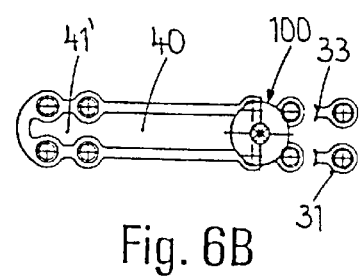
Fig. 6A  Fig. 6B
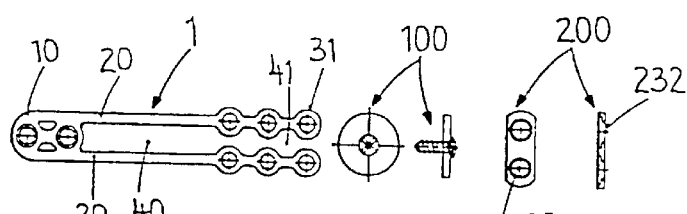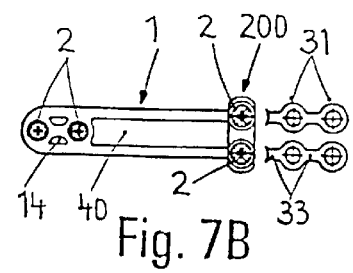
Fig. 7A  Fig. 7B

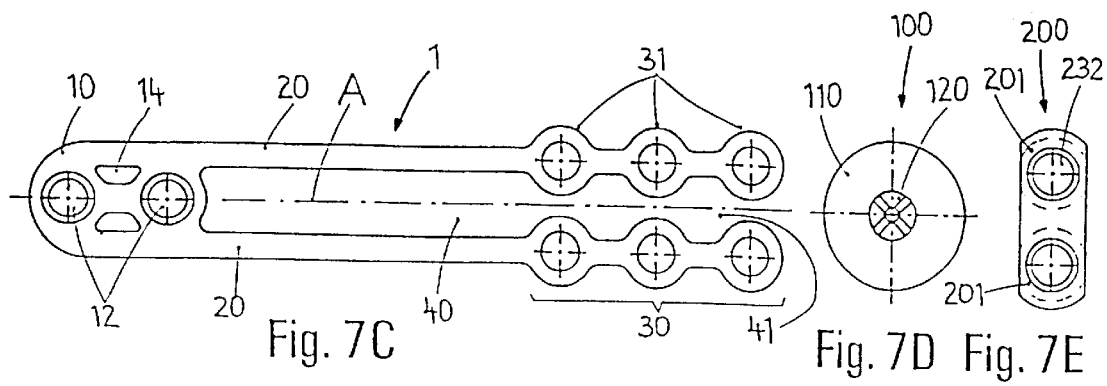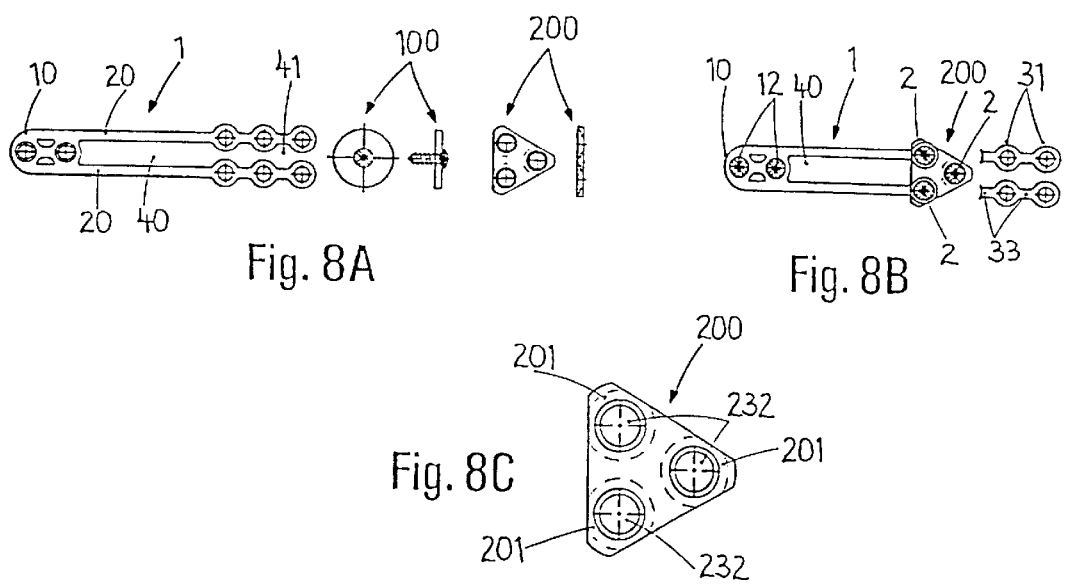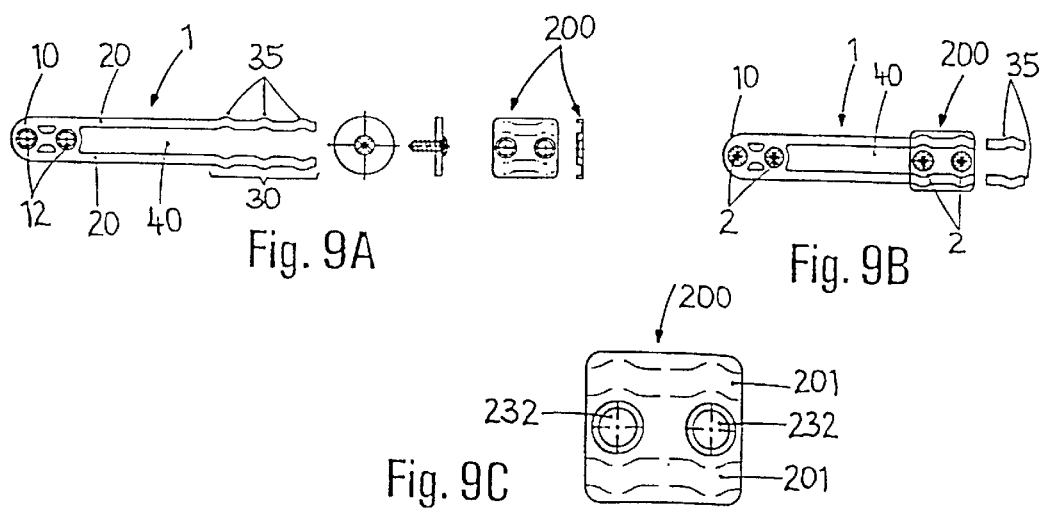

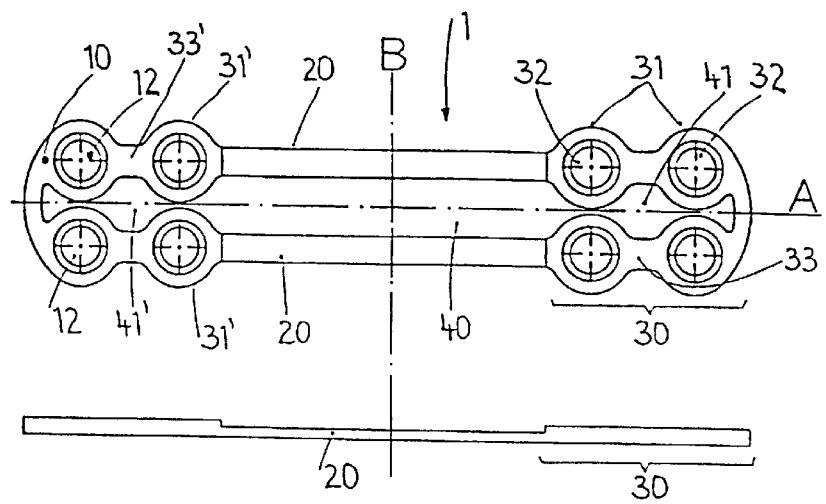
Fig. 12C
Fig. 12D
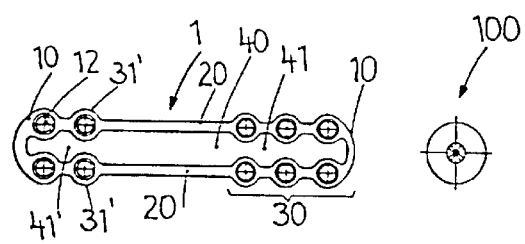
Fig. 13A
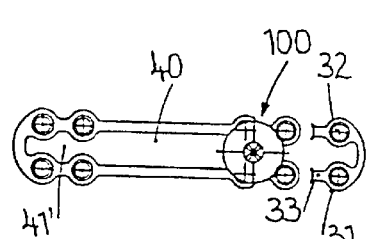
Fig. 13B
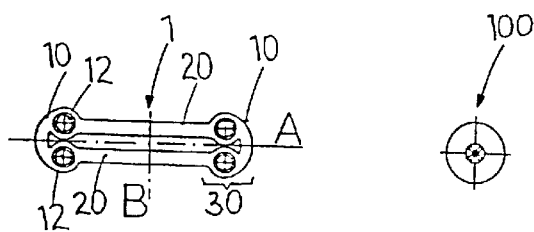
Fig. 14A
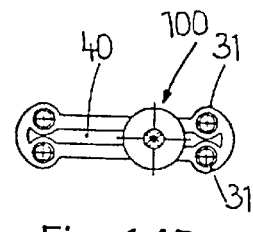
Fig. 14B
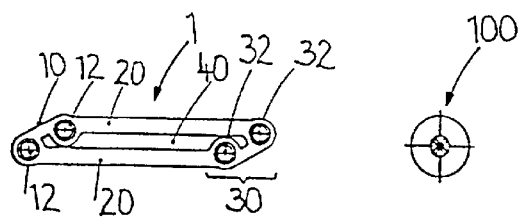
Fig. 15A
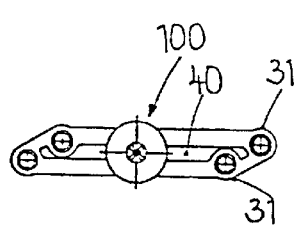
Fig. 15B

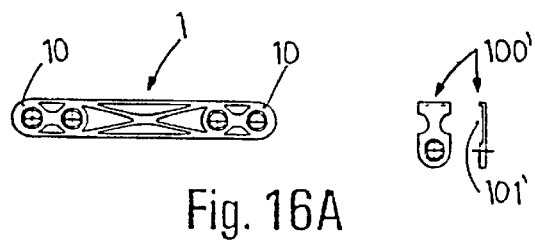 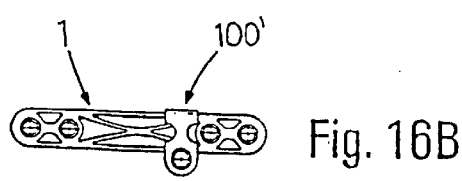
Fig. 16A
Fig. 16B
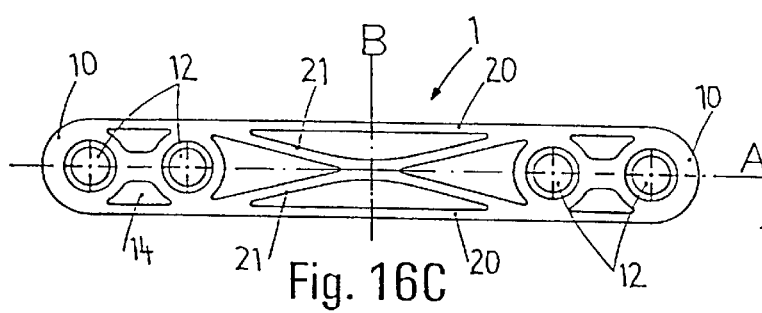 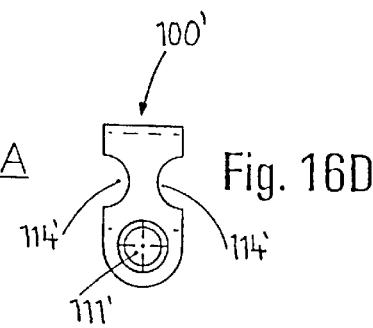
Fig. 16C
Fig. 16D
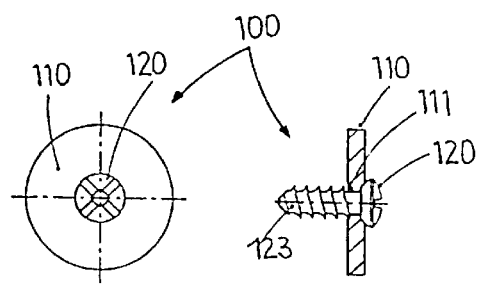 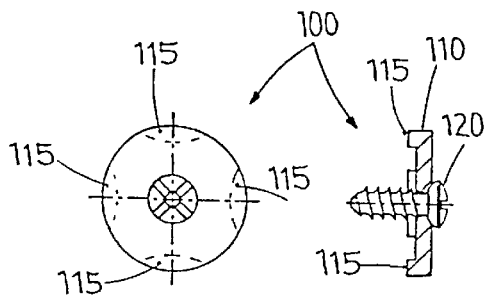
Fig. 17B  Fig. 17A      Fig. 18B  Fig. 18A
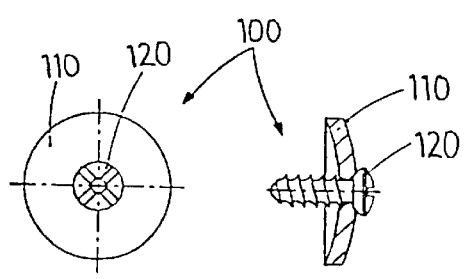 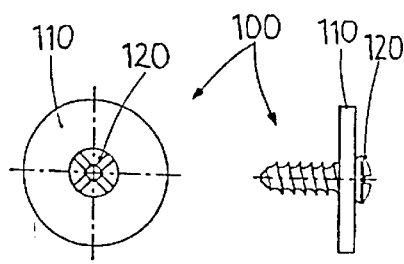
Fig. 19B  Fig. 19A      Fig. 20B  Fig. 20A
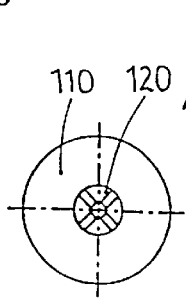 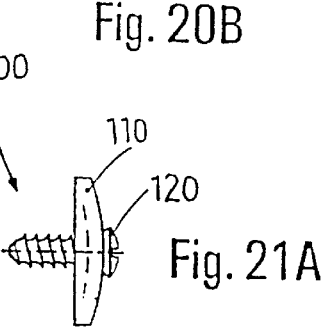
Fig. 21B  Fig. 21A

OSTEOSYNTHETIC FASTENING DEVICE

BACKGROUND OF THE INVENTION

The present invention relates to a device for osteosynthetic fixation of bone fragments, in particular of fragments of a jaw bone. Devices of this type are fitted intraoperatively in order to mutually fix bone fragments which have become separated from each other. This may be necessary either in the context of osteosynthesis, after accidents in which a bone is shattered into bone fragments, or in the context of orthognathic or maxillofacial treatment for surgical control of abnormal positioning after osteotomy and subsequent positional correction of the bone fragments. Such a device principally spans and fixes two bone fragments together, one part of the device in each case being connected releasably to a respective bone fragment. In order to create the connection between tie temporarily fitted device and the bone fragments, the bone plate (which constitutes the essential structural element of the device) has through-holes in which securing elements sit, in most cases bone screws, which engage in the bone fragments. In these devices it is important that the bone fragments are fixed in a stable manner and in the correct position relative to each other.

DESCRIPTION OF THE PRIOR ART

DE-C-23 40 880 discloses a solid compression plate which is used for treating jaw fractures and which, spanning the fracture site on the jaw bone, is screwed onto both of the bone compartments to be joined together. In each half of the compression plate there are two oblong holes oriented toward the plate center and toward the fracture site. On the side directed away from the jaw bone, the oblong holes have a countersink with a screw seat configured as a beveled plane surface. At least one oblong hole per half is inclined relative to the plate center. On the side directed toward the jaw bone, the bone plate has a projecting notched web at the center. As a result of the arrangement of the oblong holes and the bevelled screw seats, the bone compartments are compressed at the fracture site when the inserted bone screws are tightened. Because of its rigidity, this plate cannot readily be adapted to the existing bone geometry. The simple hole engagement permits little variability in terms of attachment to the bone compartments, and preliminary provisional fixing prior to final positioning is possible only within very limited ranges of movement.

A further refined bone plate for fixation of bone compartments is the subject of WO-A-97 01991. The bone plate described there has at least one continuous screw hole on both its outsides, between which screw holes there is a first axial oblong hole which is limited on both longitudinal flanks by struts lying opposite each other. Moreover, a bracket-shaped retainer is provided for engaging over the bone plate in the transverse direction, i.e. over both struts with the first oblong hole lying between them. The retainer has a second oblong hole which extends transverse to the longitudinal axis of the bone plate and thus also transverse to the first oblong hole. The longitudinal dimension of the second oblong hole corresponds to the width of the first oblong hole. The retainer has two angled guide noses on the outside facing the bone plate, which guide noses engage over and below both struts in the fitted state, so that the retainer is longitudinally displaceable on the bone plate as on a double rail.

In use, one outside of the bone plate is screwed securely to a first bone compartment. The retainer is then temporarily mounted on the bone plate in the area of the first oblong hole and is fixed by means of a locking screw inserted into the second bone compartment after positioning of the movable bone compartment. Said positioning is done by means of longitudinal relative displacement between the bone plate and the retainer within the clearance of the first oblong hole and by transverse relative displacement between the locking screw and bone plate and the retainer within the clearance of the second oblong hole. When bone plate and retainer have been fixed thus far and the bone compartments have been oriented with respect to each other, the remaining outside of the bone plate is screwed to the second bone compartment. Thereafter, the locking screw is unscrewed and the retainer is also removed.

Compared with the earlier state of the art, the bone plate described above resulted in a marked improvement since its flexibility meant that it can be adapted more easily and more accurately to the respective bone geometry. In addition to this, the retainer permits, intraoperatively, an initially approximate and then precise orientation of the two bone compartments which are to be joined together. However, the following shortcomings still remain:

a) The retainer and the associated locking screw are two relatively small and separate individual parts and their application is correspondingly awkward.

b) The length of the bone plate is fixed and is not adaptable to the particular situation. The firs longitudinal oblong hole located in the bone plate is enclosed on all sides and lies between the screw holes, as a result of which there is limited variability in terms of longitudinal mobility.

c) The bone plate can be screwed onto the bone compartments to be joined together only in the area of rigidity; greater variability would also be of advantage here.

OBJECT OF THE INVENTION

In view of the inadequacies of the devices known hitherto for osteosynthetic fixation of bone fragments with a temporarily attached retainer, the object of the invention is to configure the bone plate belonging to the device in such a way as to improve its adaptability to the particular bone situation by easier deformability, simplified choice of length and greater variability in the setting of locally variable rigidities. In addition, it is intended to provide as great as possible a range of clearance or the bone plate provisionally fixed with a retainer. It is also intended to simplify the handling of the hitherto two-part retainer and bone plate during the operation. Finally, it must be possible for the whole device to be manufactured economically in serial production.

SUMMARY OF THE INVENTION

In a first embodiment of the fixation device, the bone plate has a longitudinal guide slot which is bordered by plate struts and which is open at one end or closed at both ends. A retainer which can be temporarily attached to the bone plate comprises a disk which engages partially over the bone plate and in which a locking screw sits either in a rotatable manner or fixed, said locking screw being intended to be screwed into a bone compartment via the guide slot. The retainer and bone plate together with the respective bone compartments can be displaced relative to each other within the length and width of the guide slot. A plurality of screw holes are provided on the bone plate, at least at one end. At one end, the bone plate advantageously has an area of members comprising members which can be divided off so as to be able to obtain the desired length in each case. With several possibilities for screwing the bone plate, it is possible to achieve better adaptability to the respective task and improved rigidity across the edge of the bone plate, while the elasticity of the latter can be increased across the surface by means of less material thickness.

The disk fitted on the locking screw of the retainer is advantageously secured against dropping. By this means, an as it were one-piece retainer is obtained whose handling is simplified. A fixing plate is provided for additional stiffening of the screwed-on bone plate and/or for screwing the bone plate at one end, which fixing plate can be mounted on the bone plate screwed on at the other end with bone screws through screw holes.

In a second embodiment, the retainer attached to the bone plate has a plate which engages partially over the bone plate and which can be screwed to the underlying bone compartment laterally to the outside of the bone plate.

BRIEF DESCRIPTION OF THE ATTACHED DRAWINGS

FIG. 1A shows a plan view of a bone plate open laterally at one end, with a horizontal connection web, one area of members on each of two parallel free plate struts, and a guide slot extending between the connection web and the areas of members, and an associated retainer in plan view and side view;

FIG. 1B shows the bone plate according to FIG. 1A with a retainer fitted in the guide slot, fitted bone screws, and two symmetrically divided-off holed members;

FIG. 1C shows the bone plate according to FIG. 1A enlarged;

FIG. 1D shows the retainer according to FIG. 1A enlarged, in a partial cross-sectional side view;

FIG. 1E shows the retainer according to FIG. 1A enlarged, in a plan view;

FIG. 2A shows the representation according to FIG. 1A, with a narrowing guide slot continuing out between the areas of members;

FIG. 2B shows the bone plate according to FIG. 2A, with a retainer fitted in the guide slot between the areas of members, and two symmetrically divided-off holed members;

FIG. 3A shows the representation according to FIG. 2A, with a straight guide slot continuing out between the areas of members;

FIG. 3B shows the bone plate according to FIG. 3A, with a retainer fitted in the guide slot between the areas of members, and two symmetrically divided-off holed members;

FIG. 4A shows the representation according to FIG. 2A, with a vertical connection web;

FIG. 4B shows the bone plate according to FIG. 4A, with a retainer fitted in toe guide slot between the areas of members, and two symmetrically divided-off holed members;

FIG. 5A shows the representation according to FIG. 2A, with a kidney-shaped connection web;

FIG. 5B shows the bone plate according to FIG. 5A, with a retainer fitted in the guide slot between the areas of members, and two symmetrically divided-off holed members;

FIG. 6A shows the representation according to FIG. 5A, with a kidney-shaped connection web behind an additional pair of holed members;

FIG. 6B shows the bone plate according to FIG. 6A, with a retainer fitted in toe guide slot between the areas of members, and two symmetrically divided-off holed members;

FIG. 7A shows the representation according to FIG. 1A, with an additional strip-shaped fixing plate in plan view and side view;

FIG. 7B shows the bone plate with screwed-on fixing plate according to FIG. 7A, fitted bone screws, and four symmetrically divided-off holed members;

FIG. 7C shows the bone plate according to FIG. 1A and 7A, enlarged;

FIG. 7D shows the retainer according to FIGS. 1A and 7A, enlarged in a plan view;

FIG. 7E shows the fixing plate according to FIG. 7A, enlarged in a plan view;

FIG. 8A shows the representation according to FIG. 7A, with a triangular fixing plate;

FIG. 8B shows the bone plate according to FIG. 7B, with a screwed-on fixing plate according to FIG. 8A;

FIG. 8C shows the fixing plate according to FIGS. 8A and 8B, enlarged in a plan view;

FIG. 9A shows a plan view of a bone plate open laterally at one end, with a horizontal connection web, a guide slot extending from the connection web, and undulating free-ending plate struts, and also an associated retainer and an additional approximately square fixing plate, each in a plan view and side view;

FIG. 9B shows the bone plate according to FIG. 9A with screwed-on fixing plate according to FIG. 9A, fitted bone screws, and two strut members symmetrically divided off from the plate struts;

FIG. 9C shows the fixing plate according to FIGS. 9A and 9B, enlarged in a plan view;

FIG. 12C shows the bone plate according to FIG. 12A, enlarged in a plan view;

FIG. 12D shows the bone plate according to FIG. 12C in a front view;

FIG. 13A shows the representation according to FIG. 12A, with an additional pair of holed members at the right-hand end and with a guide slot continuing between the holed members;

FIG. 13B shows the bone plate according to FIG. 13A, with a retainer fitted in the guide slot, between the holed members, and with a symmetrically divided-off connection web;

FIG. 14A shows the representation according to FIG. 12A, without the holed members in front of the connection webs;

FIG. 14B shows the bone plate according to FIG. 14A, with a retainer fitted in the guide slot;

FIG. 15A shows a bone plate closed laterally at both ends, with connection webs arranged in the form of a parallelogram and with a guide slot extending between the connection webs, and also an associated retainer, each in a plan view;

FIG. 15B shows the bone plate according to FIG. 15A, with a retainer fitted in the guide slot;

FIG. 16A shows a plan view of a bone plate closed laterally at both ends, with horizontal connection webs and apertures provided between the connection webs, and an associated laterally fixable retainer in a plan view and side view;

FIG. 16B shows the bone plate according to FIG. 16A, with an attached retainer;

FIG. 16C shows the bone plate according to FIG. 16A, enlarged in a plan view;

FIG. 16D shows the retainer according to FIG. 16A, enlarged in a plan view;

FIG. 17A shows the retainer according to FIG. 1D, with a planar disk which is rotatable and nonreleasable on the screw shank;

FIG. 17B shows the retainer according to FIG. 17A in a plan view;

FIG. 18A shows the representation according to FIG. 17A, with a disk which has locking catches on its underside;

FIG. 18B shows the retainer according to FIG. 18A in a plan view;

FIG. 19A shows the representation according to FIG. 17A, with a curved disk;

FIG. 19B shows the retainer according to FIG. 19A in a plan view;

FIG. 20A shows a one-piece retainer with a planar disk sitting securely on the screw shank;

FIG. 20B shows the retainer according to FIG. 20A in a plan view;

FIG. 21A shows a one-piece retainer with a curved disk sitting securely on the screw shank; and FIG. 21B shows the retainer according to FIG. 21A in a plan view.

DESCRIPTION OF THE PREFERRED EMBODIMENTS

Figure 10A:
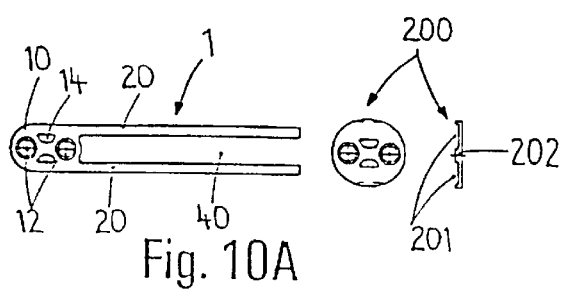
FIG. 10A shows a plan view of a bone plate open laterally at one end, with a horizontal connection web, a guide slot extending from the connections web, and straight free-ending plate struts, and, associated with this, an additional roundish fixing plate with a central web, in a plan view and side view.

A detailed description of illustrative embodiments of the fixation device according to the invention is given below with reference to the attached drawings.

The following observation applies to the whole of the following description. If reference numbers are given in a figure for the purposes of clarity but are not mentioned in the directly related text of the description, reference is made to their mention in previous or subsequent figure descriptions. In the interest of clarity, repeated mention of components in subsequent figures is in most cases omitted insofar as the drawings clearly show that these are "recurring" components.

FIGS. 1A and 1C

The fixation device consists of a bone plate 1, in this case laterally open at one end and with a horizontal connection web 10, and also of a retainer 100. Two mutually parallel and spaced-apart plate struts 20 extend from the connection web 10, and at their ends they are each provided with an area of members 30 comprising in each case three holed members 31 which lie closely opposite each other in pairs. Extending between the connection web 10 and the area of members 30 there is a guide slot 40 which in the area of members 30 is constricted to a three-times narrowed gap 41 and emerges diametrically opposite the connection web 10. The holed members 31 are eye-shaped and each have a central screw hole 32 and a transition web 33 to the adjacent holed member 31. Consequently, the central pair of holed members 31 has two diametrically opposite transition webs 33 per holed member 31, which transition webs 33 establish the connection to the inner pair and outer pair of holed members 31. The two plate struts 20 adjoin the inner pair of holed members 31 opposite the transition webs 33, while the outer pair of holed member 31 only have transition webs 33 directed toward the central pair of holed members 31. A theoretical longitudinal axis A can lie longitudinally through the bone plate 1, said bone plate 1 being symmetrical with respect to said longitudinal axis A. The connection web 10 has two screw holes 12 lying on the longitudinal axis A, between which screw holes 12 there are two apertures 14 spaced symmetrically apart from the longitudinal axis A. The apertures 14 are used for engagement of a holder instrument known per se for bringing the bone plate 1 to the application site during the operation.

The retainer 100 consists of a circular disk 110 in which a locking screw 120 sits centrally. Disk 110 and locking screw 120 can together form one part or are connected to each other in such a way that the locking screw 120 is rotatable in the disk 110 but the disk 110 cannot come loose from the locking screw 120.

FIG. 1B

The retainer 100 is intended to be mounted on the bone plate 1 which has first been screwed onto the first bone compartment. Screwing by means of bone screws 2 at one end could be carried out both or the areas of members 30 and on the connection web 10 via the screw holes 12, the latter alternative being generally followed. After rough adjustment of both bone compartments, the retainer 100 is placed on the bone plate 1 and the retainer 100 is first screwed loosely onto the second bone compartment by means of the locking screw 120 so that the bone plate 1 under the retainer 100 remains movable in order to permit fire adjustment of both bone compartments relative to each other. The locking screw 120 penetrates through the guide slot 40 and engages in the underlying second bone compartment, and the disk 110 of the retainer 100 spans the distance between both plate struts 20. For fine adjustment, relative movements between both bone compartments are therefore still possible, i.e. the bone plate 1, with the screwed-on bone compartment, and the other bone compartment with the attached retainer 100 can be moved relative to each other in the range of clearance which remains for the retainer 100 with locking screw 120 within the guide slot 40.

After fine adjustment of both bone compartments relative to each other, the locking screw 120 is tightened so that the disk 110 presses on the two plate struts 20 with a clamping effect, and the set position of he two bone compartments is thus fixed. The bone screws 2 on the connection web 10 are now introduced into the screw holes 12. If the full length of the plate struts 20 with the extending areas of members 30 is not needed, the excess number of holed members 31 can be divided off. In order to avoid sharp edges, the appended transition webs 33 are also divided off. The length in which the bone plate 1 is used, the screw holes 32, 12 which are fitted with bone screws 2, and the question of whether bending of the bone plate 1 is carried out for adjustment, all depend on the local bone geometry and on the intended end result.

When both ends of the bone plate 1 are screwed onto the two bone compartments by means of bone screws 2, i.e. in the area of members 30 and on the connection web 10, the retainer 100 has then fulfilled its temporary function. The locking screw 120 is unscrewed from the underlying bone compartment and the retainer 100 is removed from the bone plate 1.

FIGS. 1D and 1E

At the center of the circular disk 110 of the retainer 100 there is a through-bore 11 with a countersink 112 on the upper side 113 of the disk. In this illustrative embodiment, the bore 111 has an internal thread. The lower part of the screw head 122 of the locking screw 120 is partially embedded in the countersink 112. The screw shank 123 with the external thread 121 penetrates through the bore 111, said external thread 121 and internal thread of the bore 111 engaging in one another. The disk 110 therefore cannot fall from the locking screw 120. On its upper side, the screw head 122 has an engagement contour 124, in this case a circular slit, for application of a conventional screwing instrument. As will be described later (see FIGS. 17A through 21B), there are other possible ways of preventing the disk 110 from falling from the locking screw 120.

FIGS. 2A and 2B

This embodiment of the bone plate 1 differs in that the bone plate 1 as a whole is wider, so that the plate struts 20 lie farther apart and a wider guide slot 40 is obtained. Thus, the areas of members 3C with the holed members 31 on both plate struts 20 also lie farther apart, as a result of which a larger gap 41 is obtained. The guide slot 40 is as it were continued by the adjoining gap 41. This in particular permits an extended longitudinal range of clearance upon fine adjustment, since the retainer 100 can be screwed-in within an extended guide slot 40, in other words within the areas of members 30. The locking screw 120 now sits between the holed members 31.

FIGS. 3A and 3B

An extended guide slot 40 which likewise also extends via the gap 41 between the areas of members 30 has been generated here by having all the holed members 31 with screw holes 32 pointing outward, i.e. they do not protrude into the path of the gap 41, as a result of which the gap 41 has smooth edges toward the holed members 31. This also opens up the possibility of positioning the retainer 100 with locking screw 120 not only in the guide slot 40, but also, as is illustrated, in its continuation, within the gap 41.

FIGS. 4A and 4B

In contrast to FIG. 2A, the connection web 10 is arranged vertically. The two apertures 14 lie on the longitudinal axis A, while the screw holes 12 are spaced apart symmetrically from the longitudinal axis A. In the illustrative embodiment shown, the plate struts 20 with the adjoining areas of members 30 lie so far apart that once again a guide slot 40 is obtained which is extended by the gap 41. The retainer 100 can thus be positioned along the entire length of the guide slot 40 and adjoining gap 41.

FIGS. 5A and SB

As is shown here, the connection web 10 can also be given a kidney-shaped configuration. The two screw holes 12 located therein are once again spaced apart symmetrically from the longitudinal axis A; an aperture 14 lies on the longitudinal axis A. Otherwise, this embodiment is identical to the previous embodiment.

FIGS. 6A and 6B

In this alternative embodiment, the kidney-shaped connection web 10 on the bone plate 1 has been made narrower, apertures 14 have been completely omitted, and a pair of holed members 31' have been mounted in front of the screw holes 12 in the connection web 10, symmetrical with the longitudinal axis A. The additional holed members 31' extend the possibilities of securing the bone plate 1 and thus also of setting different rigidities of the bone plate 1. At one end, each additional holed member 31' adjoins one of the plate struts 20, and at the other end each holed member 31' has a transition web 33' which adjoins the connection web 10 in alignment with the plate strut 20. With sufficient distance transverse to the longitudinal axis A between the holed members 31', so that the screw shank 123 of the locking screw 120 can pass through the interspace between the pair of holed members 31' and if appropriate also through the interspace between the screw holes 12, a gap 41' is also obtained at the side of the connection web 10, which gap 41' extends the guide slot 40 in this direction as far as the connection web 10. Bone plate 1 and retainer 100 can now be displaced relative to each other along the length of the guide slot 40 and the extensions via the gaps 41, 41' at both ends. The retainer 100 is shown in its position in the gap 41 within the areas of members 30, but the bone plate 1 can also be fixed with the locking screw 120 sitting in the guide slot 40 or in the gap 41'. As in all thee previous representations, an unnecessary pair of holed members 31 and transition webs 33 are divided off from the areas of members 30 of the bone plate 1.

FIGS. 7A and 7C through 7E

The bone plate 1 and the retainer 100 correspond to the embodiment according to FIGS. 1A and 1D. A strip-like fixing plate 200 is provided to increase the rigidity of the screwed-on bone plate 1 after removing the temporarily fitted retainer 100. The fixing plate 200 has screw holes 232 which are congruent with respect to a pair of screw holes 32 arranged on both sides of the longitudinal axis A of the bone plate 1. On the underside of the fixing plate 200 directed toward the bone plate 1, depressions 201 are arranged around the outlet of the two screw holes 232, into which depressions 201 the pair of holed members 31 of the bone plate 1 come to lie.

FIG. 7B

The fixing plate 200 can be attached to the screwed bone plate 1 while the retainer 100 is still fitted. The attached fixing plate 200 spans, underneath it, the two holed members 31 lying on both sides of the longitudinal axis A, and the turned-in bone screws 2 sit with their heads on the upper side of the fixing plate 200, while the shanks of the bone screws 2 penetrate the screw holes 232 in the fixing plate 200 and also the screw holes 32 in the holed members 31 of the bone plate 1 and engage in the underlying bone compartment. As has been described above, in the screwed state the screw holes 12 in the connection web 10 are likewise fitted with bone screws 2 in order to screw this side of the bone plate 1 to the other bone compartment. In the example shown here, two pairs of holed members 31 were not needed and were divided off, each contiguous with the adjoining holed member 31, together with transition webs 33.

FIGS. 8A through 8C

Compared with the previous group of FIGS. 7A through 7E, the fixing plate 200 is now triangular and, in the third corner, which lies on the longitudinal axis A, it has a further screw hole 232 in addition to the two screw holes 232 present in the strip-shaped fixing plate 200. In order to be able to apply the fixing plate 200 correctly to the bone plate 1 in each of the three possible positions of rotation, depressions 201 are located on the underside of the fixing plate 200, at the outlets of all three screw holes 232. In the assembled state, one pair of holed members 31 of the bone plate 1 lies with its screw holes 32 congruent, under the fixing plate 200, with respect to the screw holes 232, which are screwed by means of bone screws 2. The third and as it were free screw hole 232 of the fixing plate 200 can also be used for inserting a bone screw 2, which then engages directly in the underlying bone compartment.

FIGS. 9A through 9O

The difference with this bone plate 1, laterally open at one end and with a horizontal connection web 10, is that the plate struts 20 originating at the connection web 10 end in an undulating area of members 30 and do not have any holed members 31, and the guide slot 40 thus extends from the connection web 10 to the outlet at the free ends of the plate struts 20. There are no changes to the connection web 10 or to the retainer 100; by contrast the fixing plate 200 is modified in conjunction with the modified ends of the plate struts 20. Since holed members 31 with screw holes 32 have been omitted in this case at the free end of the plate struts 20, the fixing plate 200 has, in addition to the previous stiffening function, the main function of allowing this end of the bone plate 1 to be screwed to the underlying bone compartment.

The free ends of both plate struts 20 have outwardly curving and systematically reseating bulges symmetrical with respect to the longitudinal axis A, so that on each plate strut 20 an area of members 30 is obtained comprising a plurality of strut members 35 of identical shape and lying in line. The fixing plate 200 has an approximately square configuration for this bone plate 1 and has two spaced-apart screw holes 232 lying on the longitudinal axis A. On the underside of the fixing plate 200, complementary with the shape of the areas of members 30, there are two depressions 201 which are likewise symmetrical with respect to the longitudinal axis A and which consequently extend in the direction of extent of the areas of members 30.

In the screwed state, the fixing plate 20C lies over the two areas of members 30, the latter being partially embedded in the depressions 201. By means of bone screws 2 which penetrate the screw holes 232 on the fixing plate 200 and the screw holes 12 on the connection web 10 of the bone plate 1, the latter is screwed to both bone compartments. Excess strut members 35 which are not needed are cut off from the areas of members 30.

Figure 10B:
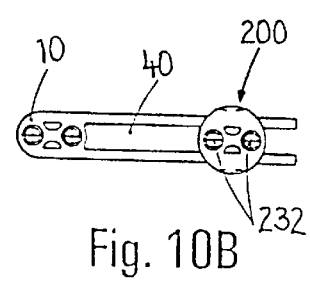
FIG. 10B shows the bone plate according to FIG. 10A with fitted fixing plate.
Figure 10C:
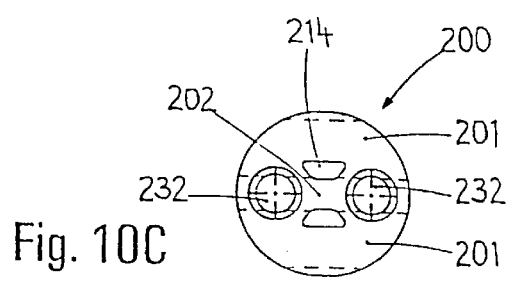
FIG. 10C shows the fixing plate according to FIGS. 10A and 10B, enlarged in a plan view.

FIGS. 10A through 10C

Here, the free ends of the plate struts 2C are designed straight and without any area of members 30, so that the guide slot 40 extends uniformly from the connection web 10 to the end of the plate struts 20. The roundish fixing plate 200 has two spaced-apart screw holes 232 which lie on the longitudinal axis A and between which there are two apertures 214 symmetrical with respect to the longitudinal axis A. The apertures 214 have the same role as the apertures 14 in the bone plate 1. On the underside of the fixing plate 200, and congruent with respect to the extent of the plate struts 20, there are two groove-like depressions 201 running parallel with the longitudinal axis A. A raised central web 202 thus remains between the depressions 201, in the axial area of the screw holes 232. The fixing plate 200 could be fitted on the plate struts 20 along the entire length of the latter, but in practice, because of the screwing of two bone compartments and the rigidity which is to be achieved, it is best to arrange the fixing plate 200 only near the ends of the plate struts 20. In the assembled state, the plate struts 20 are partially embedded in the depressions 201.

Figure 11A:
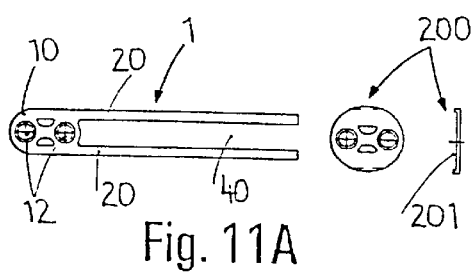
FIG. 11A shows the representation according to FIG. 10A, without the central web on the roundish fixing plate.
Figure 11B:
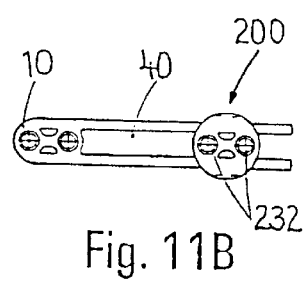
FIG. 11B shows the bone plate according to FIG. 11A, with attached fixing plate.
Figure 11C:
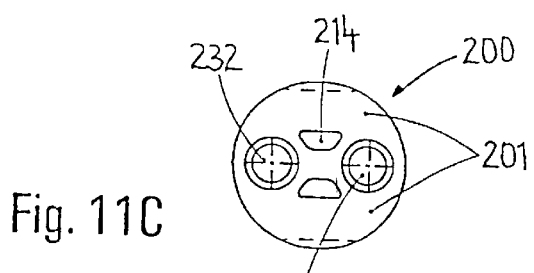
FIG. 11C shows the fixing plate according to FIGS. 11A and 11B, enlarged in a plan view.

FIGS. 11A through 11C

The only difference from the previous group of FIGS. 10A through 10C is that the depressions 201 on the underside of the fixing plate 200 are not divided by a central web 202, and instead the depression 201 extends continuously almost to the upper and lower edges of the fixing plate 200.

FIGS. 12A through 12D

The bone plate 1 is closed laterally at both ends and has kidney-shaped connection webs 10 at both ends. The left-hand connection web 10 has two spaced-apart screw holes 12 symmetrical with respect to the longitudinal axis A, and, connected to these via transition webs 33', a pair of holed members 31'. The right-hand side and the left-hand side of the bone plate 1 are identical, i.e. symmetrical with respect to a vertical axis B perpendicular to the longitudinal axis A. In order to maintain the system, an area of members 30 on the right-hand side is defined in each case by two pairs of holed members 31 which are in turn connected to each other via transition webs 33. The connection web 10 is situated on the outside. Extending between the holed members 31' and the area of members 30 is the guide slot 40 which is adjoined to the right and left by the gaps 41, 41', which are narrow, so that there is no widening of the guide slot 40. The guide slot 40 is flanked by the plate struts 20 which extend parallel with the longitudinal axis A and which connect the area of members 30 to the forward holed members 31'. The plate struts 20 have a lesser thickness than the other parts of the bone plate 1. This favors bending of the bone plate 1, from the flat configuration of the bone plate 1, adapted to the specific bone geometry. There is a higher degree of rigidity in the plane, as it were across the edge. The greater material thickness outside the plate struts 20 gives the bone screw 2 fitted into the screw holes 12, 32 a more stable fit. The retainer 100 is positioned inside the guide slot 40.

FIGS. 13A and 13B

The only difference from the previous group of FIGS. 12A through 12D is that the area of members 30 now has a third pair of holed members 31, and the holed members 31 and the screw holes 12 with the forward holed members 31' are at a greater distance from the longitudinal axis A, so that widened gaps 41, 41' are obtained which result in lengthening of the guide slot 40 at both ends. The retainer 100 is positioned inside the gap 41, and the outer unnecessary pair of holed members 31 is cut away together with connection web 10 and transition webs 33.

FIGS. 14 and 14B

Figure 12A:
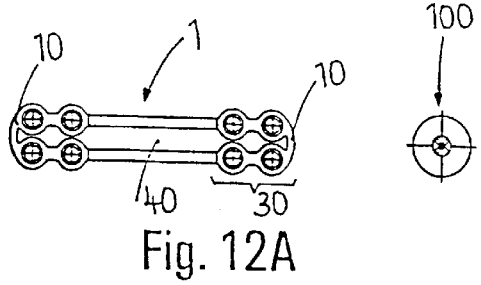
FIG. 12A shows a bone plate closed laterally at both ends, with kidney-shaped connection webs which each have a pair of holed members mounted in front of them, and a guide slot extending between the holed members, and also an associated retainer, each in a plan view.
Figure 12B:
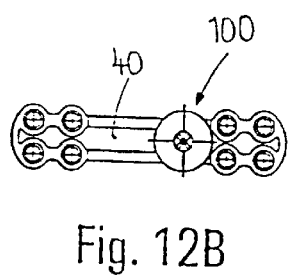
FIG. 12B shows the bone plate according to FIG. 12A, with a retainer fitted in the guide slot.

Compared with FIG. 12A, the bone plate 1 shown here is reduced at both ends by the pair of forward holed members 31' and a pair of holed members 31 from the area of members 30. The guide slot 40 (the retainer 100 can consequently only be positioned here) accordingly extends only between the area of members 30 and the screw holes 12. This bone plate 1 is of symmetrical construction with respect to the longitudinal axis A and the vertical axis 3.

FIGS. 15A and 15B

In contrast to preceding FIGS. 14A and 14B, the connection webs 10 are now no longer kidney-shaped, and instead they represent the narrow sines or a bone plate 1 having the overall shape of a parallelogram. The two screw holes 12, 32 in each case thus no longer lie on two common theoretical verticals, and each upper screw hole 12, 32 is offset to the right. The guide slot 40 in which the retainer 100 is fitted extends once again between the connection web 10 and the area of members 30.

FIGS. 16A, 16C and 16D

A bone plate 1 closed laterally at both ends, with two outer horizontal connection webs 10, and a laterally attachable retainer 100' are shown. The bone plate 1 is constructed symmetrically with respect to longitudinal axis A and vertical axis B. The connection webs 10 correspond to the embodiments according to FIG. 1A. A guide slot 40 has been dispensed with here, since the retainer 100' has the bore 111' for introducing the locking screw 120 toward the outside. To increase the rigidity of the bone plate 1, but while maintaining the bending capacity for the purpose of adaptation to the particular bone geometry, transverse reinforcement struts 21 are provided in addition to the parallel plate struts 20. The reinforcement struts 21 extend between the two connection webs 10.

The shackle-shaped retainer 100' is designed to engage over the bone plate 1 parallel with he vertical axis B and has the bore 111' on the lower periphery. The notches 114' let in on both sides are complementary to the position of the screw holes 12 so that the retainer 100' can stand near a screw hole 12 and also between two screw holes 12, without colliding with the bone screws 2 which are to be screwed in and have raised screw heads. On its underside, the retainer 100' has, above the bore 111', a groove 101', in the width of the bone plate 1 in order to partially enclose the latter from the top. The retainer 100' and the locking screw 120 (see FIG. 1A) can be two separate parts or car. form an inseparable unit. A conventional bone screw 2 can be used as locking screw 120.

FIG. 16B

In the assembled state, the bore 111' of the retainer 100' lies laterally outside the bone plate 1, so that the associated locking screw 120 can be screwed into the underlying bone compartment, but not tightened at first. A still loosely screwed-on retainer 100' once again permits the relative movements for fine adjustment of both bone compartments relative to each other. In this fine adjustment, the retainer 100' can be swivelled about the axis of the locking screw 120 and can be moved along the longitudinal axis A on the bone plate 1. After said fine adjustment, the bone plate 1 is screwed in fully and the retainer 100' is then removed.

FIGS. 17A and 17B

In this alternative, compared with FIGS. 1D and 1E, the central through-bore 111 in the circular disk 110 of the retainer 100 is not provided with an internal thread. However, in order to prevent the disk 110 from falling from the locking screw 120, the bore 111 on the disk 110 is only minimally larger than the core diameter of the screw shank 123 and at any rate smaller than the external diameter of the screw shank 123. To achieve this, it is possible to caulk or flange an initial larger bore 111, so that the screw shank 123 can be passed through first. The locking screw 120 sitting in the disk 110 thus remains rotatable and the disk 110 is secured against falling off.

FIGS. 18A and 18B

In contrast to the preceding embodiment, the disk 110 has, on its underside, four locking catches 115 offset through 90° on the outer edge. In the assembled state, two opposite locking catches 115 engage around the plate struts 20 of a bone plate 1 positioned under the retainer 100 parallel with the vertical axis B. The other two locking catches 115 lying on the longitudinal axis A penetrate into the guide slot 40.

FIGS. 19A and 19B

In contrast to the embodiment according to FIGS. 17A and 17B, the disk 110 is curved with a concave contour in relation to the point of the locking screw 120 fitted in the disk 110. In the assembled state, the curve gives a certain spring tensioning which can be advantageous for better contact pressure of the disk on the underlying bone plate 1.

FIGS. 20A and 20B

The retainer 100 could also be made in one piece, with a disk part 110 sitting under the screw head 122. When the screw part 120 turns, the disk part 110 then always turns with it.

FIGS. 21A and 21B

The retainer 100 designed as one piece now has a curved disk part 110 according to FIGS. 19A and

What is claimed is:

1. A device for osteosynthetic fixation of bone fragments, comprising:

a bone plate extending along a longitudinal axis from a first end and having two spaced-apart, longitudinally extending plate struts spanned by a connection web at the first end;

at least one screw hole in the connection web;

a guide slot being flanked on both sides by the plate struts; and a retainer for temporary attachment to the bone plate in the area of the guide slot, said retainer including a disk and a locking screw;

wherein the disk engages over the guide slot and sits on both plate struts;

wherein further the locking screw includes a screw head sitting on the upper side of the disk and a screw shank penetrating the guide slot;

wherein further the guide slot has a length along the longitudal axis and a width transverse thereto, the length being a multiple of the width and the width being a multiple of a transverse section of the screw shank, and wherein the disk and the locking screw form an inseparable unit.

2. The device of claim 1, wherein the retainer is in one piece, wherein further the locking screw consists of the screw head and the screw shank, the screw shank extending axially from the screw head; and wherein a horizontal disk part is arranged between the screw head and the screw shank.

3. The device of claim 1, wherein the retainer is in two pieces, wherein further the locking screw consists of the screw head and the screw shank, the screw shank extending axially from the screw head; wherein further a through-bore is situated in the disk, the screw shank of the locking screw penetrating via the through-bore and the screw being rotatable in relation to the disk; and wherein the disk is arranged on the screw shank in a manner secure against loss.

4. The device of claim 1, wherein the screw head has an engagement contour at its top for application of a screwing instrument; wherein further the screw shank has a free point remote from the screw head, and wherein the disk has an underside facing towards the free point of the screw shank; and wherein catches are provided on the underside of the disk, the catches partially enclosing the plate struts.

5. The device of claim 4, wherein the underside of the disk is planar in shape.

6. The device of claim 4, wherein the underside of the disk is concave in shape.

7. The device of claim 1, wherein the plate struts run out freely at a second end of the bone plate lying remote from the first end with the connection web, so that the guide slot is open as far as the second end.

8. The device of claim 7, wherein the plate struts at the second end of the bone plate have an area of members, said area of members consisting of holed members having screw holes, the said holed members being capable of being divided off per member.

9. The device of claim 7, wherein the plate struts at the second end of the bone plate have an area of members, said area of members consisting of straight strut members capable of being divided off per member.

10. The device of claim 7, wherein the plate struts at the second end of the bone plate have an area of members, said area of members consisting of strut members having systematically repeating curves, the strut members being capable of being divided off by member.

11. The device of claim 8, 9 or 10, wherein the guide slot begins on the connection web at the first end of the bone plate and terminates before the area of members at the second end of the bone plate.

12. The device of claim 1, wherein the plate struts on both sides are spanned by another connection web at the second end of the bone plate whereby the guide slot is closed at both ends of the bone plate.

13. The device of claim 12, wherein holed members are provided between the plate struts and at least one of the connection webs, and wherein at least one of the connection webs has apertures for engagement of a holder instrument.

14. The device of claim 12, wherein holed members are provided between the plate struts and the connection web at the first end of the bone plate, and wherein the guide slot begins after the holed members at the first end of the bone plate and terminates before an area of members provided at the second end of the bone plate.

15. The device of claim 14, wherein the retainer is in two pieces, wherein further the locking screw consists of the screw head and the screw shank which axially extends from the screw head; wherein further the screw shank of the locking screw protrudes through a through-bore of the retainer, the locking screw being rotatable in relation to the retainer; wherein further the retainer is arranged on the screw shank in a manner secure against loss; and wherein the screw head is provided with an engagement contour at its top for application of a screwing instrument.

16. The device of claim 15, wherein the retainer has an underside facing away from the screw head, the underside of the retainer being provided with a groove in which the bone plate is partially embedded; and wherein on the lateral sides of the retainer notches are provided which are arranged to lie complementary with the position of the screw holes provided at both ends of the bone plate.

17. The device of claim 1, wherein holed members are provided between the plate struts and the connection web at the second end of the bone plate, and wherein the connection web has apertures for engagement of a holder instrument.

18. The device of claim 1, wherein the guide slot begins at the connection web at the first end of the bone plate and terminates at a second end of the bone plate.

19. The device of claim 1, wherein a fixing plate having at least one fixing plate screw hole is provided for spanning the plate struts at a second end of the bone plate.

20. The device of claim 19, wherein said at least one fixing plate screw hole is arranged so as to come to lie between the plate struts.

21. The device of claim 19, wherein the plate. struts at a second end of the bone plate have areas of holed members having additional screw holes, wherein further said at least one fixing plate screw hole of the fixing plate is arranged to be congruent with at least one of said additional screw holes, so that a bone screw can be introduced into said congruent screw holes; and wherein on the underside of the fixing plate depressions are provided for partially embedding the holed members.

22. The device of claim 19, wherein the plate struts at a second end of the bone plate have areas of holed members having additional screw holes, wherein further said least one fixing plate screw hole of the fixing plate is arranged to be congruent with at least one of said additional screw holes, so that a bone screw can be introduced into said congruent screw holes; and wherein on the underside of fixing plate boundary webs are provided for partially embedding the holed members.

23. A device for osteosynthetic fixation of bone fragments, comprising:

a bone plate extending along a longitudinal axis from a first end to a second end and having screw holes at each of said first end and said second end;

a retainer for temporary attachment to the bone plate, the retainer having a through-bore for introduction of a locking screw fixing the retainer;

wherein the retainer engages over the bone plate transverse to the longitudinal axis;

wherein further the locking screw comprises a screw head sifting on the retainer, and wherein when the retainer is attached to the bone plate the through-bore is arranged laterally outside of the bone plate and the retainer is variably positioned along the longitudinal axis.

24. The device of claim 23, wherein the retainer and the locking screw are two separate parts.

25. The device of claim 23, wherein the retainer and the locking screw form an inseparable unit.

* * * * *